US00PP36676P2

(12) United States Plant Patent
Flore

(10) Patent No.: US PP36,676 P2
(45) Date of Patent: May 13, 2025

(54) ***PHALAENOPSIS* PLANT NAMED 'MI02651'**

(50) Latin Name: *Phalaenopsis hybrida*
Varietal Denomination: MI02651

(71) Applicant: MICROFLOR N.V., Lochristi (BE)

(72) Inventor: Febe Flore, Lochristi (BE)

(73) Assignee: MICROFLOR N.V., Lochristi (BE)

( * ) Notice: Subject to any disclaimer, the term of this patent is extended or adjusted under 35 U.S.C. 154(b) by 0 days.

(21) Appl. No.: 18/946,902

(22) Filed: Nov. 13, 2024

Related U.S. Application Data

(60) Provisional application No. 63/548,541, filed on Nov. 14, 2023.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Phalaenopsis* plant named 'MI02651', characterized by its upright plant habit; compact, semi-erect to arching leaves; strong flowering stems; freely flowering habit with typically about two inflorescences per plant, each inflorescence with numerous flowers; yellow-colored flowers with reddish purple-colored stripes and dots; and excellent postproduction longevity.

2 Drawing Sheets

Figure 1:
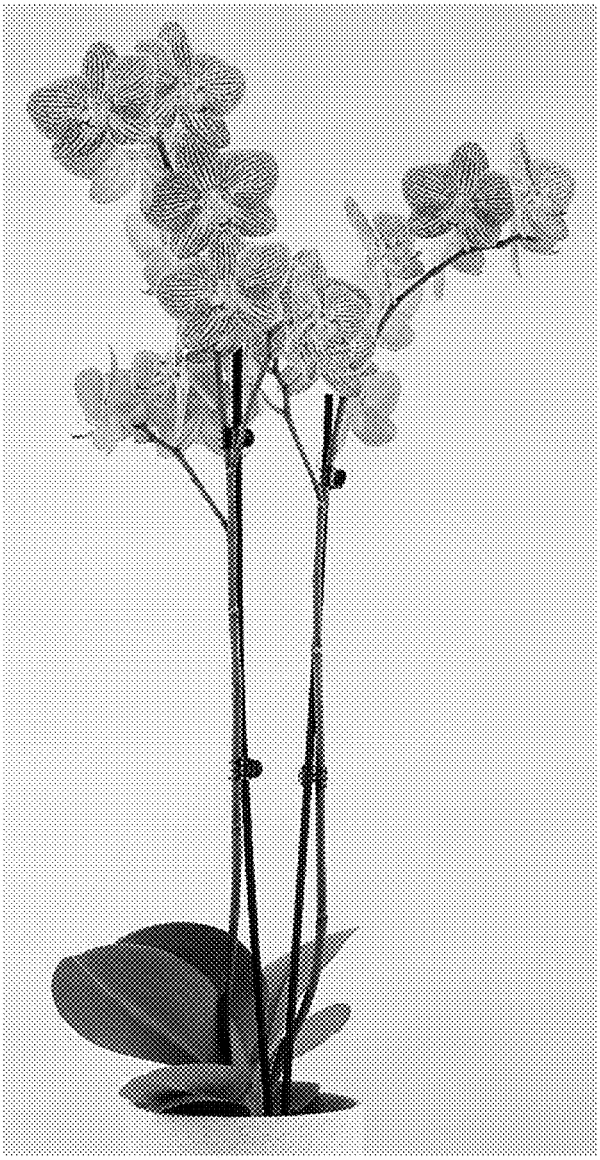

Botanical designation: *Phalaenopsis hybrida.*
Cultivar denomination: 'MI02651'.

REFERENCED TO CLOSELY-RELATED APPLICATIONS

A European Community Plant Breeder's Rights application for the instant plant was filed by the Applicant/Assignee, Microflor N.V. of Lochristi, Belgium on Sep. 12, 2023, application number 2023/1879. Foreign priority is not claimed to this application.

A Provisional U.S. Patent Application for the instant plant was filed by the Inventor and Applicant on Nov. 14, 2023, application Ser. No. 63/548,541. Domestic priority is claimed to this Provisional U.S. Patent Application.

BACKGROUND OF THE INVENTION

The present invention relates to a new and distinct cultivar of *Phalaenopsis* plant, botanically known as *Phalaenopsis hybrida*, and hereinafter referred to by the name 'MI02651'.

The new *Phalaenopsis* plant is a product of a planned breeding program conducted by the Inventor in Lochristi, Belgium. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in September 2016 in Lochristi, Belgium of a proprietary selection of *Phalaenopsis hybrida* identified as code number PHM00322, not patented, as the female, or seed, parent with a proprietary selection of *Phalaenopsis hybrida* identified as code number PH02885, not patented, as the male, or pollen, parent. The new *Phalaenopsis* plant was discovered and selected by the Inventor as a single flowering plant from within the progeny of the stated cross-pollination grown in a controlled greenhouse environment in Lochristi, Belgium in May 2019.

Asexual reproduction of the new *Phalaenopsis* plant by in vitro meristem propagation in a controlled environment in Lochristi, Belgium since December 2020 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'MI02651'. These characteristics in combination distinguish 'MI02651' as a new and distinct *Phalaenopsis* plant:

1. Upright plant habit.
2. Compact, semi-erect to arching leaves.
3. Strong flowering stems.
4. Freely flowering habit with typically about two inflorescences per plant, each inflorescence with numerous flowers.
5. Yellow-colored flowers with reddish purple-colored stripes and dots.
6. Excellent postproduction longevity.

Plants of the new *Phalaenopsis* can be compared to plants of the female parent selection. Plants of the new *Phalaenopsis* differ primarily from plants of the female parent selection in the following characteristics:

1. Plants of the new *Phalaenopsis* flower about one week earlier than plants of the female parent selection.

2. Plants of the new *Phalaenopsis* are more freely flowering than plants of the female parent selection.
3. Flowers of plants of the new *Phalaenopsis* are yellow in color with reddish purple-colored stripes and dots whereas flowers of plants of the female parent selection are yellow in color with greyed orange-colored spots.

Plants of the new *Phalaenopsis* can be compared to plants of the male parent selection. Plants of the new *Phalaenopsis* differ primarily from plants of the male parent selection in the following characteristics:

1. Plants of the new *Phalaenopsis* flower about two weeks later than plants of the male parent selection.
2. Flowers of plants of the new *Phalaenopsis* are larger than flowers of plants of the male parent selection.
3. Flowers of plants of the new *Phalaenopsis* are yellow in color with reddish purple-colored stripes and dots whereas flowers of plants of the male parent selection are white in color with violet-colored stripes.

Plants of the new *Phalaenopsis* can be compared to plants of *Phalaenopsis hybrida* 'PHALCILAK', not patented. In side-by-side comparisons, plants of the new *Phalaenopsis* differ primarily from plants of 'PHALCILAK' in the following characteristics:

1. Leaves of plants of the new *Phalaenopsis* are elliptic in shape whereas leaves of plants of 'PHALCILAK' are oblong in shape.
2. The central lobe of the labellum of plants of the new *Phalaenopsis* are trullate in shape whereas the central lobe of the labellum of plants of 'PHALCILAK' are rhombic in shape.
3. Flowers of plants of the new *Phalaenopsis* are yellow in color with reddish purple-colored stripes and dots whereas flowers of plants of 'PHALCILAK' are mostly purplish pink in color with yellow-colored centers.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'MI02651' grown in a container.

Figure 2:
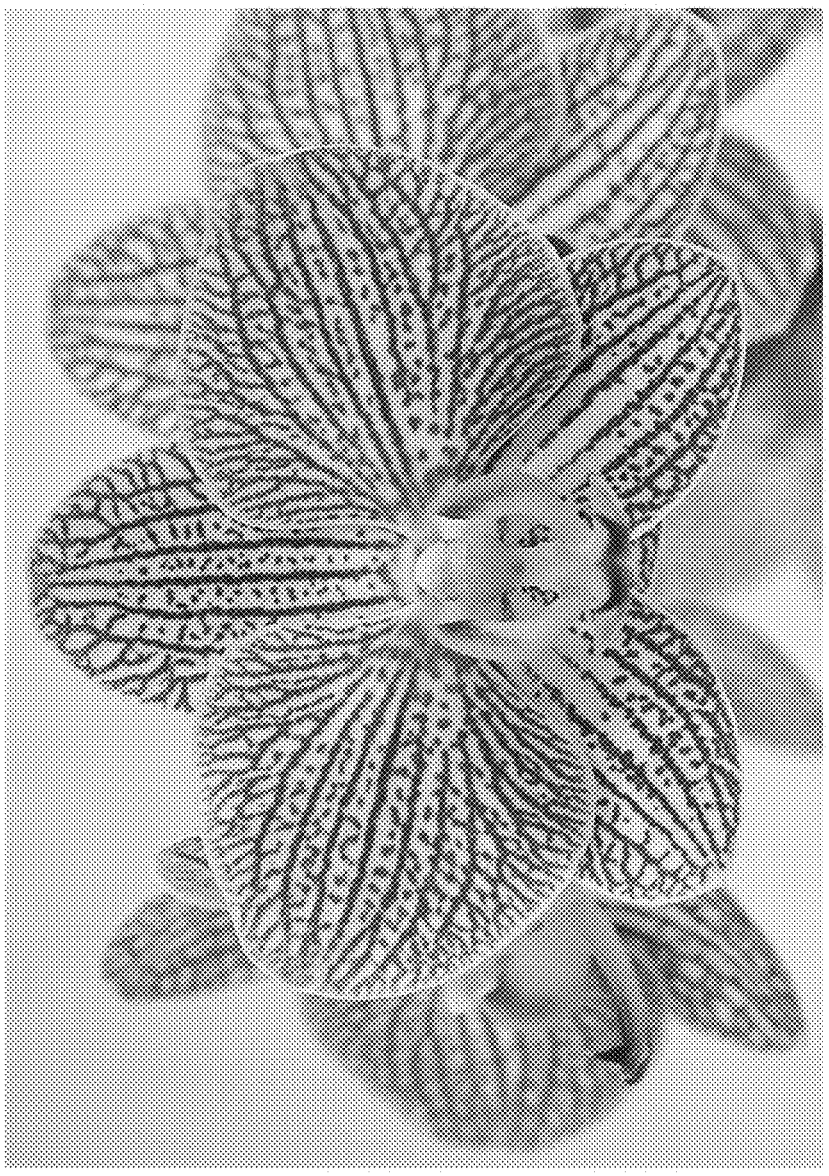

The photograph on the second sheet (FIG. 2) is a close-up view of typical flowers of 'MI02651'.

DETAILED BOTANICAL DESCRIPTION

The aforementioned photographs and following observations and measurements describe plants grown during the late summer in 12-cm containers in a glass-covered greenhouse in Lochristi, Belgium and under cultural practices typically used in commercial *Phalaenopsis* production. During the production of the plants, day and night temperatures ranged from 18° C. to 29° C. and light levels ranged from 150 Watt/m$^2$ to 375 Watt/m$^2$. Plants were 70 weeks old when the photographs and the detailed description were taken. In the following description, color references are made to The Royal Horticultural Society Colour Chart, 2001 Edition, except where general terms of ordinary dictionary significance are used.

Botanical classification: *Phalaenopsis hybrida* 'MI02651'.

Parentage:

*Female parent*.—Proprietary selection of *Phalaenopsis hybrida* identified as code number PHM00322, not patented.

*Male parent*.—Proprietary selection of *Phalaenopsis hybrida* identified as code number PH02885, not patented.

Propagation:

*Type*.—By in vitro meristem propagation.

*Time to initiate roots, summer*.—About nine to ten weeks at temperatures about 26° C.

*Time to initiate roots, winter*.—About ten to eleven weeks at temperatures about 26° C.

*Time to produce a rooted young plant, summer*.—About 140 to 160 days at temperatures about 26° C.

*Time to produce a rooted young plant, winter*.—About 150 to 180 days at temperatures about 26° C.

*Root description*.—Thick, fleshy; typically grey green in color; actual color of the roots is dependent on substrate composition, water quality, fertilizer, substrate temperature and age of roots.

*Rooting habit*.—Small amount of branching; sparse.

Plant description:

*Plant form and growth habit*.—Herbaceous epiphyte; upright plant habit with typically two inflorescences per plant, each inflorescence with numerous flowers; monopodial; vigorous growth habit and rapid growth rate.

*Plant height, substrate level to top of foliar plane*.—About 17 cm.

*Plant height, substrate level to top of inflorescences*.—About 63 cm.

*Plant diameter or spread*.—About 43 cm.

Leaf description:

*Arrangement and quantity*.—Distichous, simple; sessile; about seven leaves per plant; leaves are relatively compact.

*Length*.—About 18 cm.

*Width*.—About 9.5 cm.

*Aspect*.—Semi-erect to outwardly arching.

*Shape*.—Elliptic.

*Apex*.—Unequal obtuse.

*Base*.—Sheathing.

*Margin*.—Entire.

*Texture and luster, upper and lower surfaces*.—Smooth, glabrous; glossy.

*Venation pattern*.—Camptodromous.

*Color*.—When opening, upper surface: Close to 137B. When opening, lower surface: Close to 137C. Fully expanded leaves, upper surface: Close to 137A; venation, close to 137B. Fully expanded leaves, lower surface: Close to 137C; venation, close to 137C.

Inflorescence description:

*Appearance and flowering habit*.—Showy zygomorphic flowers arranged on axillary branched racemes; typically two inflorescences per plant; each inflorescence with about twelve flowers; flowers face outwardly on arching inflorescences supported by upright peduncles; flowers with three petals, two lateral petals and one center petal transformed into a labellum and three sepals.

*Fragrance*.—None detected.

*Time to flower*.—Plants begin flowering about 18 weeks after an inductive cooling period; flowers open about four weeks after flower buds develop.

*Flower longevity*.—Long flowering period and excellent postproduction longevity, individual flowers maintain good substance for about nine weeks on the plant; flowers not persistent.

*Inflorescence length* (*lowermost flower to inflorescence apex*).—About 19 cm.

*Inflorescence width*.—Axially, about 18 cm and radially, about 43 cm.

*Flower buds*.—Height: About 1.5 cm. Diameter: About 1.1 cm. Shape: Ovate. Color: Close to 145A.

*Flower diameter*.—About 8.8 cm.

*Flower depth*.—About 2.9 cm.

*Petals, quantity and arrangement*.—Three, two lateral petals and one center petal transformed into a labellum.

*Lateral petals*.—Length: About 3.9 cm. Width: About 3.9 cm. Shape: Flabellate. Apex: Rounded. Margin: Entire. Texture and luster, upper and lower surfaces: Smooth, glabrous, velvety; matte. Color: When opening, upper surface: Close to 4B; dense stripes and random dots, close to 78A; venation, close to 78A. When opening, lower surface: Close to 13B. Fully opened, upper surface: Close to 4D; dense stripes and random dots, close to 78A; venation, close to 78A; color does not change with subsequent development. Fully opened, lower surface: Close to 13D; color does not change with subsequent development.

*Labella*.—Appearance: Tri-lobed with two lateral lobes and a central lobe. Central lobe length: About 1.9 cm. Central lobe width: About 1.6 cm. Shape, lateral lobes: Oblanceolate; apices, obtuse; and margins, entire. Shape, central lobe: Trullate; apices, mucronate with short and narrow recurved cirrhose tips; margins, entire. Texture and luster, upper and lower surfaces: Smooth, glabrous, moderately velvety; matte. Callosities: Located at the base of the labellum and attachment point of the lateral petals; about 5 mm in length, about 4 mm in width and about 3 mm in height. Color, central lobe: When opening and fully opened, upper surface: Close to 12A; towards the base and apex, close to 78A. When opening and fully opened, lower surface: Close to 14B; towards the base and apex, close to 78B. Color, lateral lobes: When opening and fully opened, upper surface: Close to 13A; towards the base and apex, close to 78B. When opening and fully opened, lower surface: Close to 13A; towards the base and apex, close to 78B. Color, callosities: Close to 13A.

*Sepals*.—Quantity and arrangement: Three, two lower lateral sepals and one upper dorsal sepal. Length, lateral sepal: About 3.7 cm. Width, lateral sepals: About 2.6 cm. Length, dorsal sepal: About 3.8 cm. Width, dorsal sepal: About 2.6 cm. Shape, lateral sepals: Ovate. Shape, dorsal sepal: Elliptical. Apex, lateral sepals: Bluntly acute. Apex, dorsal sepal: Obtuse. Base, lateral and dorsal sepals: Acute to obtuse. Margin, lateral and dorsal sepals: Entire. Texture and luster, lateral and dorsal sepals, upper and lower surfaces: Smooth, glabrous, velvety; matte. Color, lateral and dorsal sepals: When opening, upper surface: Close to 4D; dense stripes and random dots, close to 78A; venation, close to 78A. When opening, lower surface: Close to 13B. Fully opened, upper surface: Close to 4B; dense stripes and random dots, close to 78A; venation, close to 78A; color does not change with subsequent development. Fully opened, lower surface: Close to 13B; color does not change with subsequent development.

*Peduncles*.—Length: About 59 cm. Diameter, proximally: About 5 mm. Strength: Strong, somewhat flexible. Aspect: Mostly upright. Texture and luster: Smooth, glabrous; matte. Color: Close to 137A.

*Pedicels*.—Length: About 4.3 cm. Diameter: About 3 mm. Strength: Moderately strong; flexible. Aspect: About 80° from peduncle axis. Texture and luster: Smooth, glabrous; matte. Color: Close to 145D and 2D.

*Reproductive organs*.—Androecium: Column length: About 1 cm. Column width: About 6 mm. Column color: Close to 155D. Pollinia quantity: Two. Pollinia diameter (per two pollinia): About 2 mm. Pollinia color: Close to 24A. Gynoecium: Stigma length: About 3 mm. Stigma width: About 3 mm. Stigma shape: Reniform. Stigma color: Close to 155D. Ovary length: About 1.25 cm. Ovary diameter: About 2 mm. Ovary color: Close to 2D. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures of about 30° C. and to be suitable for USDA Hardiness Zones 10 and higher.

It is claimed:

1. A new and distinct *Phalaenopsis* plant named 'MI02651' as herein illustrated and described.

* * * * *